United States Patent [19]

Miller

[11] Patent Number: 5,853,407
[45] Date of Patent: *Dec. 29, 1998

[54] METHOD AND APPARATUS FOR HAIR REMOVAL

[75] Inventor: Iain D. Miller, Charlestown, Mass.

[73] Assignee: Luxar Corporation, Bothell, Wash.

[*] Notice: The term of this patent shall not extend beyond the expiration date of Pat. No. 5,630,811.

[21] Appl. No.: 844,427

[22] Filed: Apr. 18, 1997

Related U.S. Application Data

[63] Continuation of Ser. No. 621,952, Mar. 25, 1996, Pat. No. 5,630,811.

[51] Int. Cl.⁶ ............................................ A61B 17/36
[52] U.S. Cl. ............................................................ 606/9
[58] Field of Search ................................... 606/9, 10, 14, 606/15, 16, 17, 20, 22, 23

[56] References Cited

U.S. PATENT DOCUMENTS

| | | | |
|---|---|---|---|
| 3,538,919 | 11/1970 | Meyer | 128/398 |
| 3,693,623 | 9/1972 | Harte et al. | |
| 3,834,391 | 9/1974 | Block | 606/9 |
| 4,388,924 | 6/1983 | Weissmann et al. | |
| 4,617,926 | 10/1986 | Sutton | 606/9 |
| 4,829,262 | 5/1989 | Furumoto | 330/4.3 |
| 5,059,192 | 10/1991 | Zalas | 606/9 |
| 5,217,455 | 6/1993 | Tan | 606/9 |
| 5,226,907 | 7/1993 | Tankovich | 606/133 |
| 5,258,989 | 11/1993 | Raven | 372/6 |
| 5,282,797 | 2/1994 | Chess | 606/9 |
| 5,290,273 | 3/1994 | Tan | 606/9 |
| 5,304,170 | 4/1994 | Green | 606/9 |
| 5,312,395 | 5/1994 | Tan et al. | 606/9 |
| 5,344,418 | 9/1994 | Ghaffari | 606/9 |
| 5,397,327 | 3/1995 | Koop et al. | 606/17 |
| 5,405,368 | 4/1995 | Eckhouse | 607/88 |
| 5,425,728 | 6/1995 | Tankovich | 606/9 |
| 5,474,549 | 12/1995 | Ortiz et al. | 606/9 |
| 5,486,172 | 1/1996 | Chess | 606/9 |
| 5,522,813 | 6/1996 | Trelles | 606/2 |
| 5,527,350 | 6/1996 | Grove et al. | 607/89 |
| 5,611,795 | 3/1997 | Slatkine et al. | 606/9 |
| 5,620,478 | 4/1997 | Eckhouse | 606/9 |

OTHER PUBLICATIONS

Gilchrest et al, "Chilling Port Wine Stains Improves the Response to Argon Laser Therapy" Plastic and Reconstructive Surgery Feb. 1982.

Anderson, R.R. and J. A. Parrish, "Selective Photothermolysis: Precise Microsurgery by Selective Absorption of Pulsed Radiation" *Science 220*: 524–527 (1983).

Anderson, R.R. et al., "The Optics of Human Skin", *Journal of Investigative Dermatology* 77(1):13–19 (1981).

Balles, M.W. et al., "Semiconductor Diode Laser Photocoagulation in Retinal Vascular Disease," *Ophthalmology* 97(11): 1553–1561 (1990).

Duffy, D.M., "Small Vessel Sclerotherapy: An Overview" *Adv. Dermatol. 3*: 221–241 (1988).

Garden, J.M. et al., "The Pulsed Dye Laser: Its Use at 577 nm Wavelength," *J. Dermatol. Surg. Oncol.* 13(2): 134–138 (1987).

(List continued on next page.)

*Primary Examiner*—Jennifer Bahr
*Assistant Examiner*—Sonya Harris-Ogugna
*Attorney, Agent, or Firm*—Seed and Berry LLP

[57] ABSTRACT

A laser treatment method for removing unwanted human hair includes irradiating a treatment site with post-coherent light of selected wavelength and peak power level and post duration, and repeating the post-coherent laser irradiation on one or more subsequent occasions with selected light parameters. A therapeutic treatment device has a laser and associated support elements and has a dermatology handpiece with a distance gage, a conduit for applying pressure and/or cooling to the treatment site and, optionally, cooling elements.

16 Claims, 4 Drawing Sheets

OTHER PUBLICATIONS

Goldman, M.P. and R.E. Fitzpatrick, "Pulsed–Dye Laser Treatment of Leg Telangiectasia: With and Without Simultaneous Sclerotherapy" *J. Dermatol. Surg. Oncol.* 16(4):338–344 (1990).

Goldman, M.P. et al., "Continuing medical education (Dermatologic surgery)," *Journal of the American Academy of Dermatology* 17(2 part 1): 167–184 (1987).

Miller, I.D., "Lasers in Plastic Surgery" Ph.D. Thesis, University of Strathclyde: Glasgow Scotland, 1990 (abstract).

Moretti, M. and I.D. Miller, "Laser–Based Hair Removal" Advertisment for Market Study by Medical Insight, Inc., Feb 1996.

Palomar Medical Technologies, Inc., Press Release, 8 Sep. 1995.

METHOD AND APPARATUS FOR HAIR REMOVAL

This application is a continuation application of Ser. No. 08/621,952 filed on Mar. 25, 1996, now U.S. Pat. No. 5,630,811. The contents of the aforementioned application is hereby incorporated by reference.

BACKGROUND

Human skin contains a number of appendages. Vascular and lymphatic channels provide for nutrition, healing and transport. Sweat and sebaceous glands provide respectively for thermal control and lubrication. Pigmented structures provide for sun protection. Hair follicles and individual hairs provide for insulation, protection and individual differentiation.

Growth of each hair is originated by germinative fibroblast cells in the basal layer of the epidermis. The hair grows both outwards and inwards during its growth cycle, and the follicle develops as an encapsulating pouch extending beyond the epidermis and down several millimeters in depth to the subcutaneous fat. Hair remains attached to the base of the follicle, where a capillary network develops to provide nourishment. During the anagenic growth phase, hair matrix cells divide rapidly and migrate upwards to form the shaft. A subsequent catagenic phase is marked by cessation of mitosis, and the reabsorption of the lower part of the follicle. Capillary nourishment is greatly reduced during this phase. In this or the final telogenic (resting) phase, the hair falls out and a new hair may replace it in a new growth cycle. At any particular time, approximately 10% of scalp hairs will be in telogenic mode.

The growth cycle varies with anatomical location from as little as 3 months for facial hair to as much as 7 years on the scalp. Hair in high friction pubic areas may be retained by the body as protection and may not shed at all.

The hair follicle consists of a mixture of germinative cells and melanocytes. Sebaceous cells empty into the follicle, providing a lipid-rich environment. The follicle is typically 0.1 mm in diameter and may extend to 4 mm in depth. The average hair diameter within the follicle is 60 um. Hair itself is generated as an accumulation of dead (keratinized) cells. Structurally it consists of two or three discrete layers, as shown in FIG. 1. The outer cuticle layer consists of a single layer of overlapping flat cells like the scales of a fish. This acts as a protective barrier. An inner cortex layer contains any pigment which may be present (pigment may also reside in melanocytes lining the follicle). Pigment may exist as two melanin forms. Eumelanin is responsible for brown/black coloration and pheomelanin is responsible for red/blonde coloration. Larger, fully developed terminal hairs also contain a core known as the medulla.

In the lower follicular region, a bulge is formed where the arrector pili muscle contacts the follicle. This muscle controls movement and orientation of the hair and may, under appropriate stimuli, render the hair vertical with respect to the skin surface. The bulge area has one of the fastest rates of cell division found in mammals, stimulated by growth factors from the lower papilla area.

While the hair follicle and hair contained therein function at several different levels, excess body hair does present a cosmetic problem for hirsute females. As a consequence, many individuals undergo hair removal treatments. Conventional techniques, including electrolysis, shaving, wax epilation and tweezing, are often painfull and temporary.

Electrolysis is used by an estimated 1 million women in the United States. Two techniques dominate the electrolysis field. Galvanic (DC) current can be passed down a fine needle inserted into the follicle. This converts tissue saline locally to sodium hydroxide, which destroys the follicle. Alternatively, the thermolysis technique utilizes an AC current to directly heat and thereby destroy the papilla. Some clinicians utilize a combination approach of these two electrolysis techniques. All electrolysis methods treat a single follicle at any time, in a painful procedure which can require analgesia. Disposable needles are used in this nonpermanent, time consuming, multiple treatment technique.

Several contemporary photonics techniques have been evaluated.

In 1993, Thermotrex Corporation was assigned two Hair Removal Device and Method patents (U.S. Pat. Nos. 5,226,907 and 5,425,728) based on the use of an externally applied chromophore to enhance local absorption of laser light. In these patents, a topically applied substance is said to penetrate to the full depth of the root of the follicle. The substances cited include permanent hair dyes, suspensions of carbon particles and photosensitizing compounds. A subsequent application of laser light is said to induce a photothermal reaction which destroys the follicle and a surrounding tissue area.

The compounds cited by Thermolase in their patents will probably demonstrate follicular selectivity. Many other topical compounds, and some systemic compounds, exist as candidates. Liposomal or lipophilic compounds may favor the lipid rich environment. Alternatively, solvents such as ethanol may be used to de-lipidize or re-organize the sebum, and thereby open the follicular passageways. Deposition of hydrophilic drugs may be facilitated by the action of wetting agents such as sodium lauryl sulfate, which may promote the creation of an emulsion. Particle size clearly plays a role in terms of ability to penetrate through narrow epidermal structures and along the follicular duct. The approach cited in this invention may work, although its practice involves the use of expensive laser equipment. Further, the use of topical compounds prolongs treatment and raises potential risk.

A second technique has been studied and reported by Drs. Melanie Grossman and Rox Anderson whereby single high energy normal mode Ruby laser pulses are applied to the skin in the absence of an externally applied chromophore. No issued patent has been awarded covering this work. In this method, the optical target is the melanin within the inner cortex layer and the pigment-bearing melanocytes lining the follicle. High fluences of up to 60 J/sq. cm. are utiized in large spotsizes, with short pulsewidths of the order of 150 $\mu$sec and a wavelength of 694 nm. This technique employs a number of natural phenomena to enhance effect on the deep follicular component. A large applied spotsize and high fluence allow for maximum depth of penetration. Concurrent cooling spares bulk tissue structures from the edema and general damage which can result from the use of fluences of this magnitude. Intimate index-matched contact of the custom handpiece with the tissue minimizes reflection loss. However, the short pulsewidths used in this approach are unlikely to efficiently transfer heat to the entire follicular structure. The Ruby laser is not readily capable of the requisite millisecond-domain pulses necessary to effect a true thermal mechanism.

A third approach, utilizing the Q-Switched Ruby laser, was disclosed by Nardo Zaias in his 1990 U.S. Pat. No. 5,059,192. This patent cited the use of a Q-Switched Ruby laser at 694 nm, with 3–8 mm spotsize and around 8 J/sq. cm. Pulsewidth was in the range 30–40 nanoseconds. Light energy administered in such a short pulsewidth will be well retained in the melanocytes lining the follicle. This approach will provide potential for melanocyte destruction and perhaps permanent depigmentation or destruction of the hair, but likely will not kill the follicle itself, since the pulsewidth is insufficiently long to conduct heat away from the targeted melanin granules.

Other approaches have been described.

In 1967, U.S. Pat. No. 3,538,919 was filed by R. Meyer. Meyer cited the placement of a fiber directly into the follicle into which a total of 30–40 J/cm$^2$ of light was subsequently launched. This fluence was administered over a period of 1–2 milliseconds, preferably by a normal mode Ruby or Nd:YAG laser. Use of a 50 um fiber was cited. This fiber diameter would theoretically fit into a 100 um follicle containing a 50 um hair, but with some difficulty. Also, the technique would be time consuming to administer, on a single hair-by-hair process.

In 1970, Richard Harte filed U.S. Pat. No. 3,693,623, which also cited the placement of a fiber directly into each follicle to be destroyed. The light source here was a xenon lamp, which applied up to 3 mJ to each follicle, in an interval of less than 3 msec. This technique again addresses each hair individually in a tedious and difficult to administer process.

In 1973, Carol Block filed U.S. Pat. No. 3,834,391, which similarly addressed the placement of a fiber at the follicular entrance. Light source was unspecified. This patent introduced the concept of the use of mineral oil, said to facilitate light conduction, presumably by index matching. No additional chromophore was added. This technique in this patent calls for the destruction of each hair on an individual basis in a tedious and difficult to administer process.

In 1981, H. Weissman filed a patent, later granted as U.S. Pat. No. 4,388,924. This cited the devitalization of hair by the specific destruction of the papillary blood supply. A narrow beam from an Argon laser was directed onto the tissue. This light was said to be absorbed by the papillary plexus, causing heating and coagulation. Multiple 20–30 millisecond exposures from a 0.5–2.5 Watt beam were cited. The hair was subsequent tweezed from its follicle. This method suffers again from the individual hair-by-hair approach, which is time consuming. Also, the selective destruction of the papillary plexus is unlikely to be practical using a narrow beam Argon laser, with its limited penetration depth capabilities, since this supply resides at several millimeter depth and is shielded by the overlying follicular structure. Indeed, no vascular specific lasers are likely to exhibit adequate dermal penetration.

In 1984, A. Sutton filed a patent, later granted as U.S. Pat. No. 4,617,926. This provided for the use of a fiber without a core, into which an individual hair slides by 2–3 mm, completing the waveguiding action. Different probes were cited, and about 1 Joule of energy launched into the fiber, from an unspecified laser source. In an alternative embodiment, the fiber is sharpened and inserted directly into the follicle. This technique is time consuming and tedious and is likely to result in rapid probe destruction.

SUMMARY OF THE INVENTION

The present invention comprises a laser treatment method and apparatus for the removal of unwanted hair.

The treatment method, according to one embodiment of the invention, includes:

Irradiation of the skin uniformly with peak power level in the range 1–500 Watts of coherent light, pulsewidth 1–99 milliseconds, spotsize 1–3 mm, and wavelength in the range 650–1000 nm, controlling the parameters until desired endpoints are observed during treatment, consisting of 'curling' or residual hair, perifollicular edema, erythema, blanching and purpura.

Allowing the skin to heal for a period of 1–3 months.

Irradiating on 0–8 subsequent occasions with additional exposures.

One apparatus for practicing the foregoing embodiment consists of:

A modified high power semiconductor diode laser system with pulsewidth variable from 1–99 milliseconds together with an adjunctive cooling apparatus and method of applying suction or pressure to better differentiate and flatten follicular structures.

The invention incorporates a modified laser apparatus with new application, together with a novel treatment method for the eradication of unwanted hair. The specific target for the laser radiation is the melanin within the hair shaft and within the melanocytes lining the follicular duct. Pulsewidth is controlled for a direct thermal effect from a single pulse. The new treatment method thus developed presents the potential for numerous significant advantages relating to the induction of precise localized thermal damage with highly penetrative coherent light. Damage thereby induced should be permanent and selective. Also, the apparatus cited in the invention has lower cost and greater portability than alternative apparatus, thus presenting cost and convenience advantages to potential patients.

This development of a clinically effective therapeutic treatment using a carefully controlled modified laser apparatus with associated minimization of adverse effects is a major improvement and advance over current options.

BRIEF DESCRIPTION OF THE DRAWINGS

For a fuller understanding of the nature and objects of the invention, reference may be made to the following detailed description and the accompanying drawings, in which.

DESCRIPTION OF ILLUSTRATED EMBODIMENTS

Figure 1:
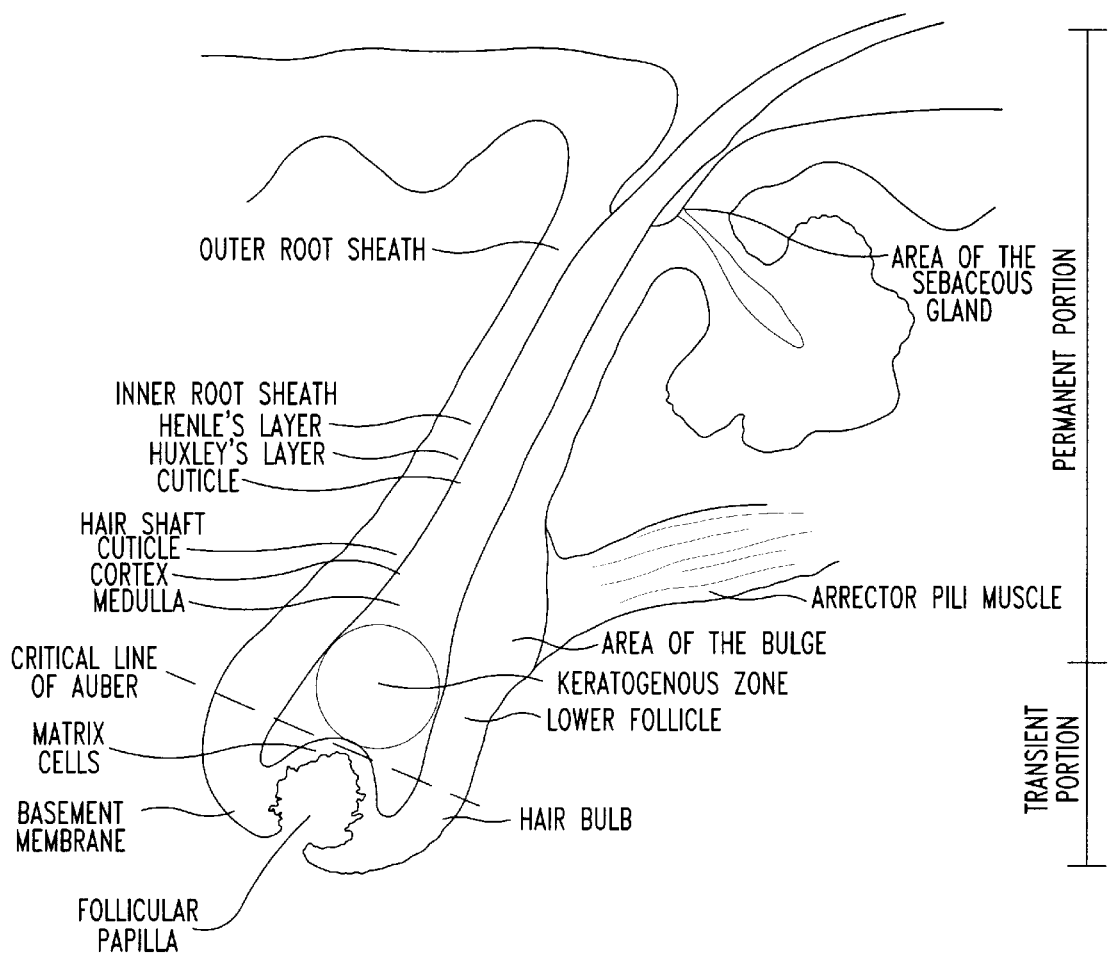
FIG. 1 is a sketch of the anatomy of a Hair Follicle.

The follicle represents a well defined physical target, which may be assumed to extend to a depth of approximately 4 mm, with a mean diameter of 100 μm. The hair within the follicle may have a diameter up to 60 um. The follicle and contained hair are well differentiated optically by melanocytes and melanin granules, which constitute the direct target in this invention.

It is necessary to consider the optical properties of the constituent skin layers and follicular components in order to assess the impact of the proposed treatment in context.

The skin is a complex, highly dynamic, variable and multi-layered optical medium. Chromophores tend to be confined to discrete structures which may be considered as having a discrete location, but scattering centers tend to be distributed uniformly throughout this optically turbid media. The dominant chromophores are melanin and the hemoglobins. Melanin is found in the basal layer of the epidermis, usually in a uniform distribution, although cellular activity of melanocytes can vary dramatically by anatomical region or between individuals. Melanin is also found in melanocytes lining the hair follicle and within individual hairs, giving them their characteristic color. The hemoglobins, being blood borne, may be considered to be relatively uniformly distributed throughout the dermis, although discrete upper and lower horizontal plexi are found in the papillary and reticular dermis respectively. Local blood (hemoglobin) concentration may be enhanced around proliferative structures, such as the hair follicle, any malignant or benign growth, or around a wound healing zone.

Optical transport processes within the skin include reflection (specular and diffuse), absorption and scattering.

In the highly turbid media of skin, many scattering events occur and this process plays a significant role in the definition of final absorption location.. Scattering results from inhomogeneities in a medium's refractive index, corresponding to physical inhomogeneities such as the collagen and elastin fibers and vascular channels. The nature of the scattering process is highly dependent on the dimensions of the scattering center. Where scattering centers are of dimension significantly less than 1 um, the scattering is weak and isotropic, or onmidirectional. This Rayleigh scattering, as commonly found in skin, results in an apparent spreading of the incident beam. Where scattering dimensions approximate beam wavelength, Mie scattering dominates, producing a much stronger, forward directed scattering, although still at some angle, usually within about 30' of the incident beam. Mie scattering is dominant in skin at visible wavelengths. When the dimension of the scattering center greatly exceeds the wavelength of the light, Fresnel reflection occurs, and a proportion of the incident photons may undergo a reversal in direction or reflection event. Reflection is a form of scattering, characterized by transitions between regions of macroscopically different refractive index.

With multiple such scattering events, the individual photons may have their directions reversed or significantly altered, resulting in a much less well defined beam as depth into tissue progresses. The process has a wavelength dependence. In broad terms, shorter 'blue' wavelengths are impacted by scattering to a greater extent, since they approximate the dimension of the scattering centers and experience Mie scattering. Longer 'red' wavelengths experience the weaker Rayleigh scattering and are less affected.

Figure 2:
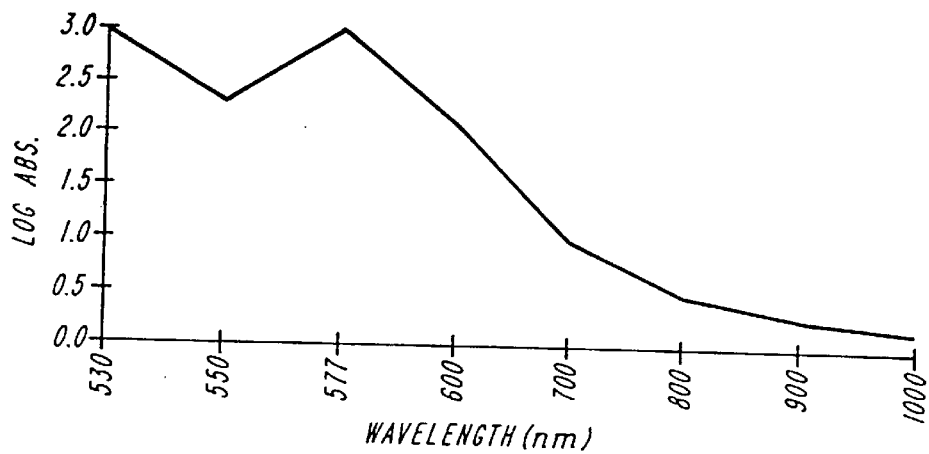
FIG. 2 is a graph of the absorption characteristics of whole blood, a local chromophore.
Figure 3:
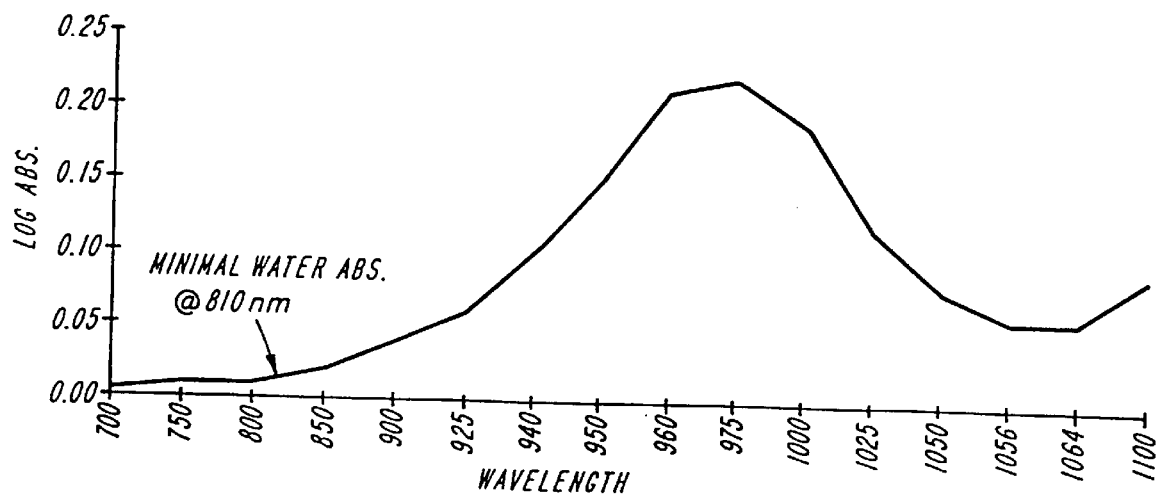
FIG. 3 is a graph of the absorption characteristics of water, a local chromophore.
Figure 4:
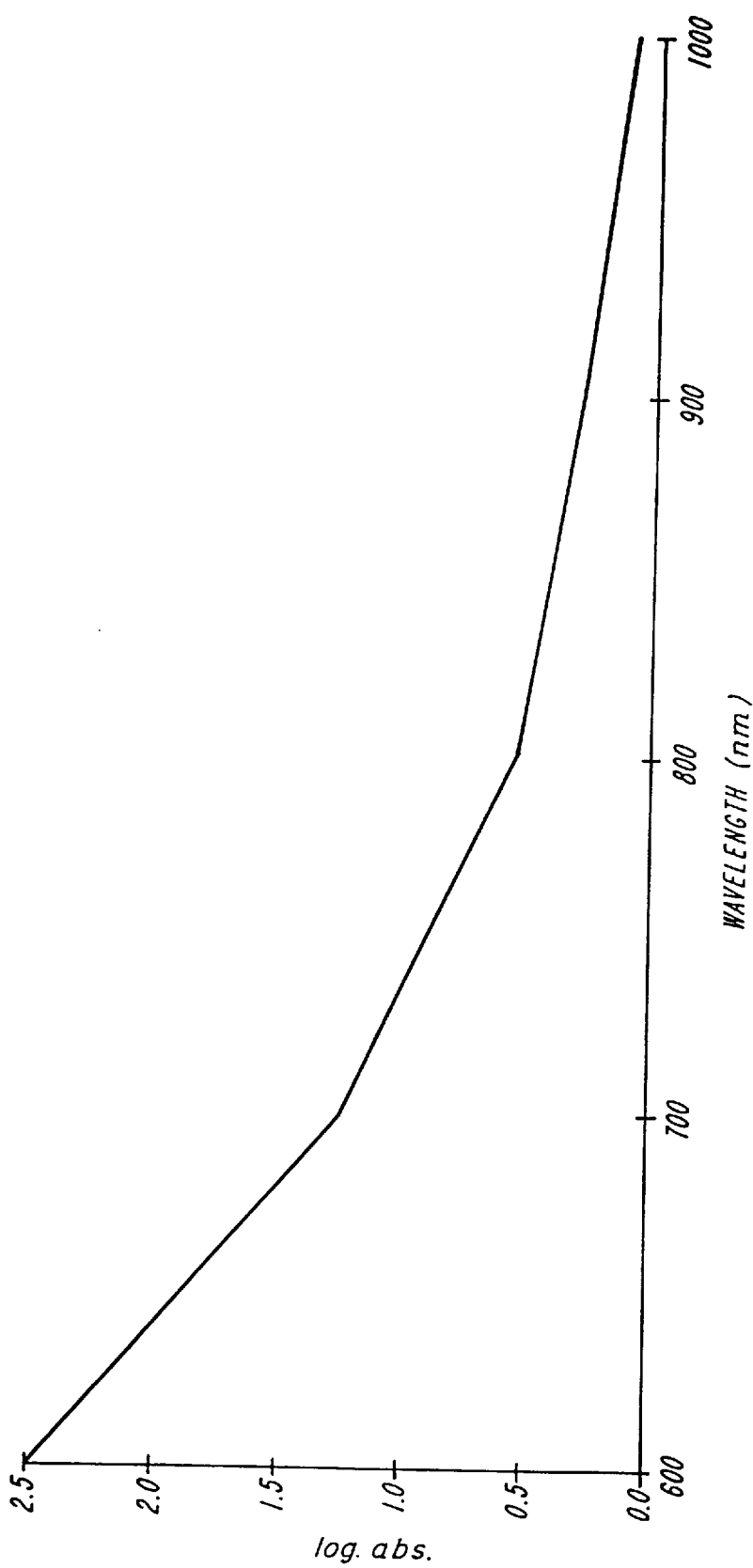
FIG. 4 is a graph of the absorption characteristics of melanin, the target chromophore.

Absorption is dominated by the hemoglobins and melanin. (Tissue water plays an insignificant role in the spectral region of interest from 650–1000 nm). As shown in FIG. 4, melanin has a monotonically decreasing absorption profile from the ultraviolet region to the near infra-red region, where absorption becomes virtually negligible around 1000 nm. The hemoglobins also tend to have an absorption characteristic which decreases towards the infra-red, though with localized absorption peaks corresponding to molecular and atomic transitions. Oxy-hemoglobin has absorption peaks around 430, 540 and 577 nm, while de-oxygenated hemoglobin has absorption peaks around 450 and 560 nm. FIG. 2 shows the absorption characteristics of whole blood, which is considered to be partially oxygenated, at the 80% level. Other blood borne chromophores include bilirubin, which has a broad absorption band around 450 nm, and beta-carotene, with a broad absorption band in the region 450–500 nm.

In terms of optimizing penetration and selective absorption within skin, the emphasis of this invention is on the minimization of scattering and unwanted absorption. Such considerations assume particular importance in hair removal, where deep-lying structures are targeted. An optical window, with minimal absorption and scattering, exists between 600–1000 nm, where depth of penetration extends to several mm. This region also exhibits selective absorption locally within the melanocytes lining the follicle and in the melanin within the hair itself, since melanin has residual absorption in this region. The region around 800–850 nm is particularly useful, as it possesses significant melanin absorption, with minimal competitive absorption from water and blood components. This region is cited in the preferred embodiment of this invention.

Thermal considerations are also significant. Given the average 100 $\mu$m dimension of the follicle, an exposure duration was derived by the inventor to induce mechanical or thermal effects. The most selective thermolysis will occur when exposure time is less than the characteristic thermal conduction time constant of this target. Exposure times significantly shorter than this may result in a mechanical process, while significantly longer exposures will result in heat transfer to the surroundings. For uniform absorption in a 100 $\mu$m dimension target such as the hair follicle, the thermal conduction time (calculated by $T=d^2/4 \times K$, where K=thermal diffusivity) may be calculated as 19 msec. During the course of this relaxation time interval, heat will spread to affect a 100 $\mu$m region around the follicle. This number provides a useful estimate of the transition range from photo-mechanical containment to proximal photo-thermal effect, although exposure intervals somewhat shorter than this time constant may still result in a thermal mechanism. In broad terms, a sub-millisecond exposure will result in conduction of less than 20 $\mu$m and a mechanical effect, while a 1–30 millisecond exposure will likely result in a specific localized thermal effect within the follicle and surrounding structure, to a radius of 20–120 um. A longer exposure will extend the thermal damage further into the peri-follicular dermis. This may occasionally be desirable, as when larger hairs are being exposed.

Calculation of Thresholds for Selective Damage

It is illustrative to calculate the necessary fluence level at which the skin area around the follicle should be exposed in order to effect the coagulative necrosis of the follicular structure. This calculation is undertaken by the inventor in the material that follows. Several assumptions are necessary. These relate to exposure time, target characteristics, and laser wavelength. In the process of the calculations, an optical distribution by absorbed tissue segment is first derived. This may be converted to a thermal distribution by means of the formula:

temperature rise=$E/C \times M$ where E=energy deposited in tissue segment=no. of photons×photon energy C=specific heat capacity of tissue M=mass of absorbing tissue segment.

It is assumed here that a temperature rise of at least 42° C. is required, representing an increase from 38° C. to 80° C. Tissue structures will undergo coagulative necrosis at this temperature for millisecond-domain exposures.

It is further assumed that melanin is uniformly distributed across the follicular dimension and that any light impinging on the follicle at the irradiating wavelength (in the region 650–1000 nm) will be completely absorbed in a uniform fashion across the dimension.

It is assumed that 20% of the incident energy from each exposure pulse within a (nominal) grid of contiguous 3 mm spots is absorbed in the follicle.

Three specific instances are presented below:

Firstly, a single 1 millisecond exposure will be considered. During this time interval, heat will spread a distance of 20 µm away from the absorbing location, assuming no phase change of the media. Hence, if the initial absorbing location is assumed to have a cross sectional diameter of 100 µm, a total width of tissue of 140 µm will be affected. If length is 2 mm, volume of heated site is 0.000043 cm$^3$. Its mass is 0.000043 g.

In order to undergo a temperature rise of at least 42° C., this tissue volume must absorb at least 0.0077 Joules of energy. Hence, the 3 mm beam spot must impart 0.038 Joules of energy within the 1 millisecond exposure, since only 20% of the incident light is usefully absorbed. This implies that the beam should have a peak power of over 38 Watts.

Secondly, a single 5 millisecond exposure will be considered. Here, radius of conduction would increase to 100 um, and affected mass of absorbing site to 0.000062 cm$^3$. This larger volume would need an irradiation of at least 0.055 Joule in this 5 millisecond period. Peak power would then need to be over 10 Watts.

Thirdly, if a 20 millisecond exposure were employed, radius of conduction would increase to 100 um, and affected mass of absorbing site to 0.00009 g. This larger volume would need an irradiation of at least 0.079 J in this 20 millisecond period. This implies that the beam should have a peak power of at least 4 Watts.

Figure 5:
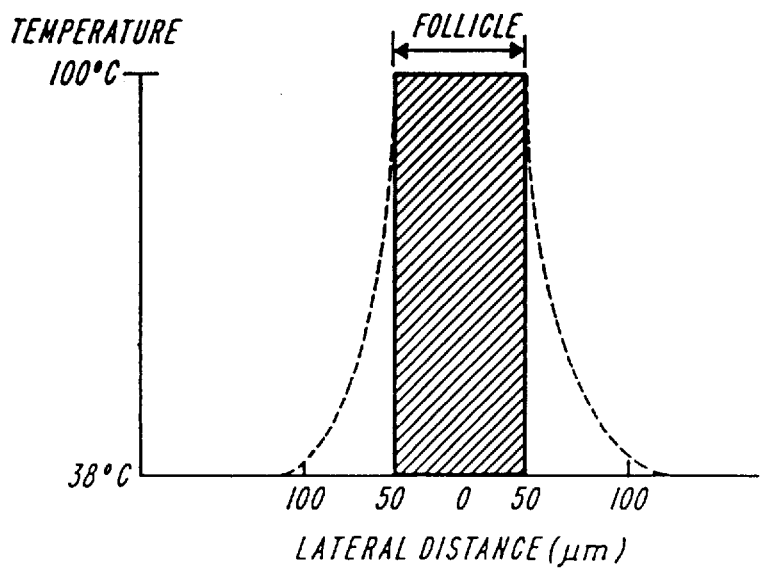
FIG. 5 is a sketch illustrating the anticipated thermal effects associated with the application of millisecond-domain near infra-red light on the follicle.

In practice, the peak powers cited above may be low for a number of reasons. Firstly, hair follicles may absorb less than 20% of the incident light, especially where the structure is lightly pigmented. Secondly, it may be necessary to involve more than 2 mm of the follicular length. Thirdly, a temperature rise of more than 42° C. may be required. Taken together, these factors may demand more than twice the peak power values calculated previously. The table below shows the likely power range as a function of irradiation pulsewidth. Precise optimum pulsewidth is not known under all circumstances, but is likely to be in the range 1–20 milliseconds, based on the preceding argument. For illustrative purposes, the effect on a hair follicle of a 50 Watt, 5 millisecond pulse is shown in FIG. 5. This plot illustrates that the absorbing follicle achieves a peak temperature of 100° C., where it is anchored. (Significantly higher incident energy would be required to impart the necessary latent heat to ensure a phase change). The dotted line in this figure shows the thermal damage envelope extending out by 50 µm radially.

The table below shows suggested useful power ranges, based on the inventor's calculations, to produce the desired specific thermal effect.

| exposure pulsewidth (msec) | peak power range for follicular necrosis (Watts) |
|---|---|
| 1 | 38–100 |
| 5 | 11–28 |
| 20 | 4–10 |

Note: A wavelength in the region of 650–1000 nm is assumed. This light will uniformly irradiate the tissue, by means of carefully placed contiguous spots, applied manually or with an automatic scanner. Uniform absorption is assumed across the follicular dimension. The values shown are illustrative only and do not capture all embodiments of the invention.

From the above theoretical analysis, it has been found a coherent laser source emitting in the wavelength region 650–1000 nm, with variable pulsewidth and spotsize capabilities, meets the conditions required for removal of unwanted hair by means of the coagulative necrosis of the follicular structures.

In the calculations above, it is understood that a typical follicular structure may be selectively damaged by use of a power level of up to 100 Watts, and an exposure pulsewidth preferably in the range 1–20 milliseconds. To allow for modeling limitations, that a source with up to 500 Watt peak power capability and pulsewidth variability in the range 1–99 milliseconds is deemed preferable to provide clinical flexibility.

The invention is further refined by addition of means to better differentiate the follicular structure. The first such means stimulates the arrector pili muscle group, which controls the angle at which the hair rests. In response to external stimuli such as cold, this muscle group will orient the hair in a perpendicular fashion. This is desirable as it allows for more uniform exposure of the entire follicular structure to the incident light. Accordingly, the invention incorporates a method for the reduction of skin temperature prior to exposure to effect this re-alignment of the hair. This further allows for desirable cooling of the superficial skin layers.

It is also desirable to reduce the apparent depth of the follicle, since this depth presents a limitation in terms of the ability of the light to impact the entire follicular pathway. This may be achieved by means of the application of suction or pressure, which draws the hair towards the skin surface or flattens local skin structures. This has the further advantage of temporarily restricting local blood flow and its competitive characteristics in terms of light absorption.

Apparatus

It was determined, in accord with the invention, that some manifestation of diode laser technology is of providing the requisite parameter set.

Semiconductor diode laser technology, first developed in 1962; today finds application in devices ranging from consumer electronics and communications to medicine.

A basic system, in the high power configuration envisaged here, has as core components an electronic power supply coupled to a semiconductor crystal encapsulated in an optical chamber capable of capturing and harnessing optical emissions from the crystal. When a large direct current is passed through the crystal, optical emission is generated and amplified. A beam of light results, with a high degree of brightness and directionality.

The basic system is further refined by means of the addition of thermo-electric cooling circuitry for temperature stabilization and of electronic circuitry for exposure control and pulsewidth generation. Maintenance needs are minimal, with a 5000+ hour life on the sources equating to several years of use.

Individual diode elements have limited output power capability and beam shapes which are not amenable to ease of delivery to distant sites. Recent efforts have concentrated on beam shaping and combination of beams from a plurality of single elements. Each single element can deliver up to 1 Watt of CW power. Under certain circumstances, higher peak power may be obtained from each diode if higher current is driven through the diode for a short period of time at a low duty cycle. For example, a diode element rated for 1 Watt CW may be driven at 2 Watts for a millisecond domain exposure period.

As a consequence, by means of the combination of beams from many such elements on diode bars, it is now possible to deliver tens or hundreds of watts of diode laser light through flexible fiber optical cable to a distant site. These high power levels as recently demonstrated by other inventors have made possible the new treatment concept outlined previously, in which such a source, appropriately modified, may be used for the current application.

A number of medical device companies have packaged diode laser systems for medical use, based on the above core subcomponents. Use of their finished systems is advocated for urology, gynecology, general and plastic surgery, gastroenterology and ENT. None of these applications involves the direct targeting of the follicular structure.

Diode laser systems as described above have been utilized for general surgical applications on soft tissue, whereby a non-specific cutting action results from the delivery of long pulses of light (>100 milliseconds pulsewidths are available from the devices), with power levels in the range 1–60 Watts. In this mode, such a device acts as an optical scalpel, with some associated coagulative potential. Shorter pulsewidth selective surgery has not been explored by medical manufacturers of this technology.

One embodiment of the invention involves the modification of such a system by means of electronic control circuitry to obtain shorter pulsewidth (1–99 millisecond) operation.

The practice of the invention harnesses the specific targeting potential of the device by means of a careful control and administration of the parameters as modeled previously. By this means, light is to pass through overlying tissue, affecting mainly the desired target follicular structures. Direct targeting of hair follicles with a high peak power (~1–500 Watts) and short pulsewidth diode source has never previously been reported.

The apparatus is further refined in the invention by addition of means to better differentiate the follicular structure. For example, the hair typically resides at an angle controlled by the arrector pili muscle group. In response to external stimuli such as cold, this muscle group will orient the hair in a perpendicular fashion. Such orientation allows for more uniform exposure of the entire follicular structure to the incident light. Accordingly, the invention incorporates a method for the reduction of skin temperature prior to exposure. This further allows for desirable cooling of the superficial skin layers. The method employed in the apparatus incorporates a cooled handpiece or cooled flowing gas.

It is also desirable to reduce the apparent depth of the follicle, since this depth presents a limitation in terms of the ability of the light to impact the entire follicular pathway. This is achieved in the invention by means of the application of suction or pressure, which flattens tissue structures or draws the hair towards the skin surface. This has the further advantage of temporarily restricting local blood flow and its competitive characteristics in terms of light absorption. A positive or negative pressure is applied in the apparatus by means of a gaseous duct within the handpiece, and gas flow originating from the main console. An inert gas may be employed, which may be cooled, further improving the treatment by reducing the risk of combustion associated with laser light.

The invention consists of a clinical treatment methodology for the eradication of unwanted body hair, described in the next section. The treatment method employs modified specific optical apparatus which is described in this section in terms of preferred and alternative embodiments. The combination of parameters described below is deemed unique and advantageous for Hair Removal.

One preferred specification for the device is listed below:

| | |
|---|---|
| Host material: | GaAs semiconductor laser source |
| wavelength range: | 800–850 nm |
| pulsewidth: | 1–99 milliseconds |
| power level: | 1–500 Watt, 1 Watt increments |
| repetition rate: | 1–20 Hz. |
| spot size on skin: | 1–3 mm, variable |
| delivery system: | fiber, with dermatology handpiece termination |
| handpiece: | thermoelectrically cooled, with flowing gas ports |
| laser cooling method: | thermoelectric |
| skin cooling method: | cooled gas (may be inert) and/or cooled handpiece |
| pulsing method: | electrical |
| aiming beam: | red diode or helium neon laser (0.5–10 mW) |
| skin treatment method: | may employ a scanner to enhance uniformity |

This preferred embodiment can specifically be utilized for the removal of unwanted hair.

A second alternative embodiment utilizes a different semiconductor material variant producing a wavelength in the range 650–1000 nm, with a peak power level in the range 1–500 Watts.

A third alternative embodiment utilizes a second host material 'pumped' by the diode laser. This host material, which itself would then lase at a different wavelength, might consist of a polymer encapsulated dye material, or some other glass or crystal structure doped with lasing ions.

All of the envisaged embodiments produce red or near infra-red light with pulsewidths and power levels amenable to the treatment of the targeted follicular structures as calculated previously.

Figure 6:
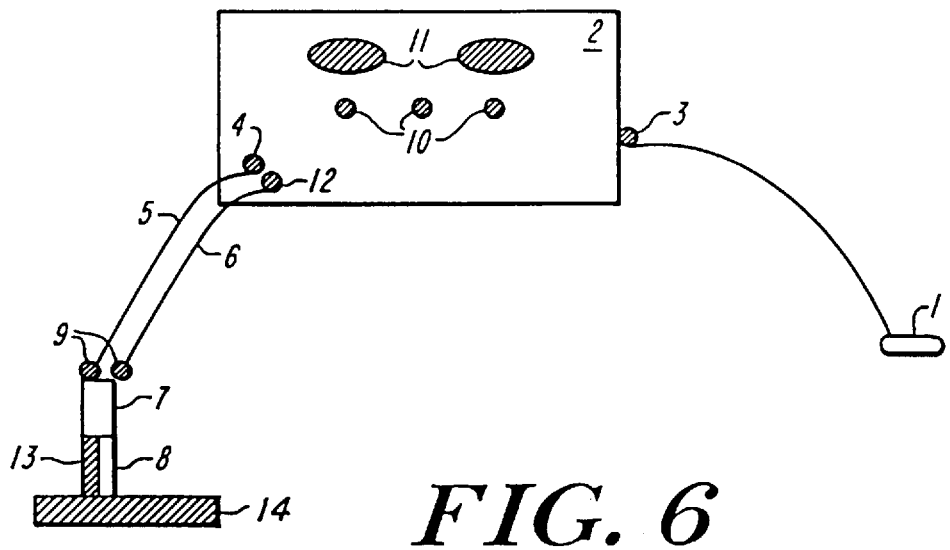
FIG. 6 is a schematic representation of the preferred treatment apparatus according to one embodiment of the invention.

This first preferred embodiment is shown in FIG. 6.

The system consists of a set of arrays of individual laser diodes contained within a compact cabinet (2). The cabinet also contains electronic and temperature control components. Triggering of pulses is provided via a separate footswitch (1) adjoined to the main console at a connector (3). Light from the internal diodes is collected internally in a set of individual small diameter fibers constituting a bundle. This bundle is grouped together physically within the cabinetry enclosure. Light transmitted through the bundle or fiber may be coupled via a high efficiency connector (4) into a single larger diameter fiber or light guide (5). A separate cooling tube (6) adjoins the fiber or light guide to provide chilled gas or water to the handpiece (7), which may separately be thermo-electrically cooled. This tube and the light guide join the handpiece at two ports (9). The cooling tube (6) allows for the application of positive or negative pressure by means of cooled gas or liquid. The cooling tube adjoins the cabinet at a junction port (12). The optical delivery media is coupled into a handpiece (7) containing focusing lenses. These lenses, together with a distance gauge (8), provide precise positioning and focusing onto the patient's skin (9). The handpiece (7) may itself be chilled by means of flowing chilled water or by use of a miniature thermoelectric element. One of the handpiece ports (9) allows for the application of a positive or negative pressure to the skin via a contact tube (13) which may be sealed. Power level, repetition rate, and pulsewidth of the source are controlled by means of several electronic controls (10) which together provide access to the specification set derived previously. Displays (11) permit verification of the selected parameter set.

An incorporated visible 'aiming beam', within the cabinetry enclosure, also delivered through the light guide, provides verification of the ultimate placement of the invisible treatment laser spot.

Clinical Treatment Methodology

The goal of the treatment is to irreversibly damage the follicular structures while leaving the surrounding normal skin intact and unaffected. Below is presented an optimal and novel therapeutic treatment methodology suitable for use in a variety of different clinical applications.

A number of major advantages and conveniences are provided by the present treatment method, including:

1. The present methodology envisages the use of a specific parameter set chosen to provide optimum selectivity of damage to the target tissue only. The damage is thermal in nature, calculated as necessary to effect a degree of controlled conduction to surrounding structures. The epidermis and peri-vascular dermis are spared while damage is administered, in a controlled fashion, uniformly throughout the targeted follicular structures. This is turn minimizes any complications associated with wound formation or unwanted cosmetic outcome.

2. All hairs within the irradiated area are treated simultaneously, eliminating the need for a tedious individualistic approach.

3. The invention provides for the use of narrow-band coherent infra-red light. Such light is able to penetrate deep into the dermis with minimal scattering or competitive absorption and affect most of the follicular structure.

4. The equipment used to provide the therapy can be manufactured at relatively low cost and has great ease of portability. This will ultimately result in greater patient access to the therapy.

5. The procedure is relatively gentle and painless, and obviates the use of multiple painful and non-permanent electrolysis treatments.

6. Several treatments are required. Each treatment will provide an occasion for the physician to tailor the parameters to the individual needs of the patient. Hence, the personal health, safety and cosmetic appearance of the skin are affected only to the extent required, and any side effects minimized.

General Treatment Procedures and Preferred Details

A power level in the range 1–500 Watts is used, with 50 Watts of peak power being a 'typical' value. An associated spotsize of 1–3 mm is applied uniformly over the entire affected tissue region. Uniformity may be enhance by means of a laser scanner, providing for a controlled pattern of exposure on the skin. A Pulsewidth in the range of 1–99 milliseconds will typically be used, with a value of 5 milliseconds being commonly selected. A wavelength in the range 800–850 nm is preferred.

Hair within the site to be treated is counted, photographed and shaved before treatment. Desirable endpoints during treatment include some curling of the remaining exposed hair shaft.

After treatment, the site may be somewhat blanched (whitened) due to some coagulation of follicular appendages. Some fine purpura may also be present, as a result of some absorption by localized blood vessels, which will be coagulated.

An assessment will be made at the second visit relating to any color or texture change of the skin. The vessel itself will also be graded for any lightening. Absence of any lightening or adverse effects will be taken as indicative of the need to increase energy or exposure time. Occurrence of significant adverse sequellae will be taken as indicative of the need to decrease power and exposure parameters.

Detailed Protocol

The site to be treated is photographed under controlled conditions and a hair count attempted. It is further examined to detect the presence of scarring or otherwise abnormal color or texture. Exposed hair is shaved.

On the first treatment visit, individual portions of the site to be treated are designated as test sites to which different carefully chosen parameters of laser light are applied. An initial set of parameters would typically be: 30 Watts of light, 2 mm spotsize, 1 millisecond exposure time. Different sites within the designated area may be exposed with different power levels or pulse durations. Some additional useful parameter combinations include use of 30 Watts with 3 or 5 milliseconds exposure time. Lower power levels may be used with longer exposure times, such as the combination of 10 Watts with 5 or 20 milliseconds. Feedback is obtained from each application in terms of immediate tissue response and used to determine subsequent test site parameters. Desired response includes a 'curling' of any remaining hair above the skin. If tissue damage is evident, power level and/or pulsewidth may be decreased. If the desired endpoints of hair curling and local mild edema are not observed, power level and/or exposure time may be increased.

Following treatment, a topical antibiotic ointment may be applied to the treated site and the skin area covered with a dressing.

The patient will return after a specified healing period (usually 1–3 months) for evaluation and further treatment. These additional treatments (typically up to 7) are administered with the parameters found to result in minimal regrowth with minimal adverse sequellae. Parameters are adjusted if the response is inadequate (insufficient hair growth retardation) or too severe (induration, ulceration or pigmentary change to the overlying epidermis). In the former case, applied power and/or pulsewidth is increased, while in the latter case it is decreased.

If a site has not responded (in terms of a reduction of hair count or growth delay) after a total of 6 treatments, treatment is to be discontinued. In any event, the patient should be followed for up to one year to note any incidence of recurrence.

I claim:

1. A laser treatment method for the removal of unwanted hair from the skin of a human, said method comprising the steps of irradiating on a first occasion a treatment site comprising a chosen section of human skin containing at least one hair growing within a hair follicular structure with pulsed coherent light with wavelength in the range 650–1000 nm, said light having a peak power level in the range 1–500 Watts and a pulse duration of 1–99 milliseconds and said diameter of treatment beam being in the range 1–5 mm;

allowing the skin to heal for a period of 1–3 months;

irradiating the treatment site on each of a set of subsequent occasions with pulsed coherent light with a wavelength in the range 650–1000 nm, said light having a peak power level of 1–500 Watts and a pulse duration of 1–99 milliseconds and said diameter of treatment beam being in the range 1–5 mm; and pre-cooling the treatment site, such that damage to the skin tissue surrounding the hairs is minimized.

2. The laser treatment method in claim 1, wherein pre-cooling the treatment site includes application of chilled water or gas.

3. The laser treatment method in claim 2, further comprising the step of aligning the hairs vertically, such that damage to the skin tissue surrounding the hairs is minimized.

4. The laser treatment method in claim 2, further comprising the step of flattening local tissue structures by application of positive or negative pressure, thereby restricting local blood flow, such that damage to the skin tissue surrounding the hairs is minimized.

5. The laser treatment method in claim 2, further comprising the steps of aligning the hairs vertically, such that damage to the skin tissue surrounding the hairs is minimized; and flattening local tissue structures by application of positive or negative pressure, thereby restricting local blood flow, such that damage to the skin tissue surrounding the hairs is minimized.

6. The laser treatment method of claim 1, wherein pre-cooling the treatment site includes direct thermoelectric cooling of a handheld laser device.

7. The laser treatment method in claim 6, further comprising the step of aligning the hairs vertically, such that damage to the skin tissue surrounding the hairs is minimized.

8. The laser treatment method in claim 6, further comprising the step of flattening local tissue structures by application of positive or negative pressure, thereby restricting local blood flow, such that damage to the skin tissue surrounding the hairs is minimized.

9. The laser treatment method in claim 6, further comprising the steps of aligning the hairs vertically, such that damage to the skin tissue surrounding the hairs is minimized; and flattening local tissue structures by application of positive or negative pressure, thereby restricting local blood flow, such that damage to the skin tissue surrounding the hairs is minimized.

10. The laser treatment method of claim 1, wherein pre-cooling the treatment site includes application of chilled water or gas and direct thermoelectric cooling of a handheld laser device.

11. The laser treatment method in claim 10, further comprising the step of aligning the hairs vertically, such that damage to the skin tissue surrounding the hairs is minimized.

12. The laser treatment method in claim 10, further comprising the step of flattening local tissue structures by application of positive or negative pressure, thereby restricting local blood flow, such that damage to the skin tissue surrounding the hairs is minimized.

13. The laser treatment method in claim 10, further comprising the steps of aligning the hairs vertically, such that damage to the skin tissue surrounding the hairs is minimized; and flattening local tissue structures by application of positive or negative pressure, thereby restricting local blood flow, such that damage to the skin tissue surrounding the hairs is minimized.

14. The laser treatment method in claim 1, further comprising the step of aligning the hairs vertically, such that damage to the skin tissue surrounding the hairs is minimized.

15. The laser treatment method in claim 1, further comprising the step of flattening local tissue structures by application of positive or negative pressure, thereby restricting local blood flow, such that damage to the skin tissue surrounding the hairs is minimized.

16. The laser treatment method in claim 1, further comprising the steps of aligning the hairs vertically, such that damage to the skin tissue surrounding the hairs is minimized; and flattening local tissue structures by application of positive or negative pressure, thereby restricting local blood flow, such that damage to the skin tissue surrounding the hairs is minimized.

* * * * *